United States Patent [19]

Baucom et al.

[11] 4,374,715
[45] Feb. 22, 1983

[54] METHOD FOR THE PREPARATION OF POLY (CARBONOYL FLUORIDE) OLIGOMERS

[75] Inventors: Keith B. Baucom, Gainesville; Burrell N. Hamon, Starke, both of Fla.

[73] Assignee: The United States of America as represented by the Secretary of the Air Force, Washington, D.C.

[21] Appl. No.: 274,697

[22] Filed: Jun. 17, 1981

[51] Int. Cl.$^3$ ............................................. B01J 19/12
[52] U.S. Cl. ............................................... 204/158 R
[58] Field of Search ........................ 204/158 R, 158 N

[56] References Cited

U.S. PATENT DOCUMENTS

| 2,575,125 | 11/1951 | Prober | 260/82.1 |
| 2,700,661 | 1/1955 | Miller | 260/87.5 |
| 3,442,942 | 5/1969 | Sianesi et al. | 260/544 |
| 3,706,773 | 12/1972 | Anello et al. | 260/408 |
| 3,896,167 | 7/1975 | Sianesi et al. | 260/544 F |
| 4,003,941 | 1/1977 | Craford et al. | 260/463 |

Primary Examiner—Howard S. Williams
Attorney, Agent, or Firm—Donald J. Singer; William J. O'Brien

[57] ABSTRACT

An improved method for synthesizing poly (carbonyl fluoride) oligomers by using bis(trifluoromethyl)trioxide as a reaction initiator in the photo-oxidation of F-3 methylbutene-1.

2 Claims, No Drawings

METHOD FOR THE PREPARATION OF POLY (CARBONOYL FLUORIDE) OLIGOMERS

STATEMENT OF GOVERNMENT INTEREST

The invention described herein may be manufactured and used by or for the Government for governmental purposes without the payment of any royalty thereon.

BACKGROUND OF THE INVENTION

This invention relates to poly (carbonyl fluoride) oligomers and to an improved method for their preparation. In a more particular aspect, this invention relates to the photo-oxidation of F-3-methylbutene-1 in the presence of bis(trifluoromethyl)trioxide as a reaction initiator to form poly (carbonyl fluoride) oligomers.

s-Triazines having perfluorinated polyether substituents of the type illustrated by the following general formula:

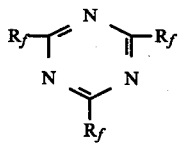

where $R_f = CFXCF_2O(CFXCF_2O)_nCFX$ and $x = CF_3$ or F. These triazines have been found to be particularly useful as candidates for high temperature fluids which serve as base stocks for advance hydraulic fluids, coolants, gas turbine engine oils and greases. These fluids possess very desirable properties such as inherent stability at temperatures up to 700° F., excellent compatability with metals up to 650° F., good lubricity and non-flammability. These characteristics make these fluids excellent candidates for a wide temperature range, non-flammable, hydraulic fluid. However, the low temperature rheological properties and moderately high volatility of these fluids have been their only deficiencies. These deficiencies can be improved, however, by increasing their oxygen to carbon ratio (o/c). This increase in o/c ratio can be accomplished by the use of poly (carbonyl fluoride) oligomers. The use of these materials involves disadvantages, however, because of the low yield of selected oligomers and their low molecular weight when produced by prior art methods of synthesis.

In an attempt to overcome the problems associated with prior art methods, it was found that the photo-oxidation of F-3-methylbutene-1 in the presence of ultraviolet radiation using a low pressure mercury lamp produced the desired oligomers with only an insignificant amount of fluoroformate terminated material being produced as a reaction by-product. In previously known methods of synthesis, fluoroformate terminated material was produced in significant amounts and had to be removed before the oligomers could be utilized in the synthesis of the desired s-triazine high temperature fluids. The oxidation of F-3-methylbutene-1, however, overcame this problem. Nevertheless, further attempts at improving the synthesis of these desirable oligomers was undertaken and a continuing research effort was maintained. As a result of this effort, it was found that the rate of the photo-oxidation reaction of F-3-methyl-butene-1 could be unexpectedly increased twofold by utilizing a minor amount of bis(trifluoromethyl) trioxide as a reaction initiator. This increase in reaction rate further increased the utilization of these oligomers in the synthesis of the s-triazine fluids.

SUMMARY OF THE INVENTION

In accordance with this invention, a novel route for the synthesis of poly (carbonyl fluoride) oligomers has been found. This novel synthesis constitutes a decided improvement in the previously known method of synthesizing poly (carbonyl fluoride) oligomers through the oxidation reaction of F-3-methylbutene-1 in the presence of ultraviolet radiation. This reaction is more fully described in U.S. patent application Ser. No. 274,574, filed of even date herewith, now U.S. Pat. No. 4,356,070. The decided improvement referred to above results from the use of bis(trifluoromethyl)trioxide as a reaction initiator in minor amounts. The use of the initiator was found to increase the rate of reaction time of the oxidation reaction twofold.

Accordingly, the primary object of this invention is to provide a simple and efficient route for the synthesis of poly (carbonyl fluoride) oligomers.

Another object of this invention is to provide faster reaction times for the photo-oxidation of F-3-methylbutene-1.

Still another object of this invention is to provide a novel method of preparing poly (carbonyl fluoride) oligomers through the photo-oxidation of F-3-methylbutene-1 in the presence of bis(trifluoromethyl)trioxide as a reaction initiator.

The above and still other objects and advantages of the present invention will become more readily apparent upon consideration of the following detailed description thereof.

DESCRIPTION OF THE PREFERRED EMBODIMENTS

With the above-defined objects in mind, the present invention involves a novel method for preparing poly (carbonyl fluoride) oligomers which find particularly utility as reaction components in the synthesis of s-triazine based hydraulic fluids. The s-triazines which have perfluorinated polyether substituents have been found to be particularly adaptable in the synthesis of thermally and oxidatively stable fluids having a wide variation in their fluid properties. These materials have the following general structure

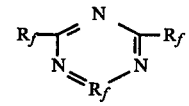

where $R_f = CFXCF_2O(CFXCF_2O)_nCFX-$ and $X = CF_3$ or F.

Perfluoroalkylene oxide s-triazines, for example, have been successfully used as hydraulic fluids. These triazines are essentially of two types; those having substituents derived from hexafluoropropylene oxide (HFPO) and those with substituents derived from tetrafluoroethylene oxide (TFEO). In general, the hexafluoropropylene oxide-derived mono-triazines have good viscosity characteristics but relatively high pour points. The opposite is true with the tetrafluoroethylene oxide-derived triazines, which have adequately low pour points but too low viscosities. An important finding of the experimental work associated with these materials is that their low temperature properties are directly related to the carbon-oxygen ratio of the triazine molecule. For a given molecular weight, the lower the carbon-oxygen ratio, the lower is the pour point of the fluid. It becomes obvious, therefore, that any improvement in the rheological properties of the triazine fluids require a lower carbon to oxygen ratio. This has been accomplished, in the past, by the preparation and utilization of carbonyl fluoride oligomers of the type illustrated by structure II in the following equations and to the synthesis of the corresponding triazines.

(I)

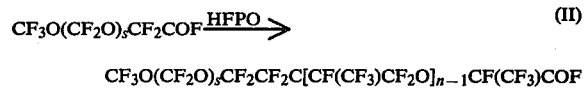

(II)

The accumulated data on HFPO terminated carbonyl fluoride triazines derived from oligomers of structure II indicates that the incorporation of relatively small amounts of the oligomers greatly improves the low temperature properties of the triazine fluids.

Unfortunately, there are major drawbacks in the preparation of the triazine fluids of this nature because of the low yields obtained in the preparation of the oligomer reactants and the experimental difficulty in adding more than one HFPO capping group. As a result of this, a major research effort has evolved devoted to finding more economical and efficient ways of preparing the carbonyl fluoride oligomer acid fluorides used in the preparation of s-triazine fluids. As a result of this research effort, it was found that poly (carbonyl fluoride) oligomers could be prepared through the photo-oxidation of F-3-methylbutene-1 using oxygen and ultraviolet radiation. A low pressure mercury vapor lamp was utilized to provide the radiation for this gas phase reaction. The mechanism postulated for the oxidation of F-3-methylbutene-1 is given below:

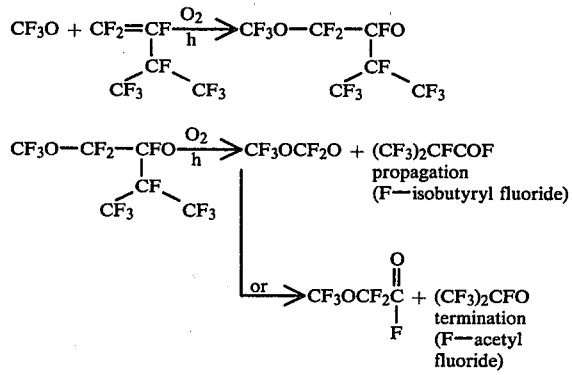

One molecule of F-isobutyryl fluoride is formed for each $CF_2O$ unit incorporated in the growing chain. One molecule of F-acetyl fluoride is formed when a radical chain is terminated. The static gas phase photo-oxidation of F-3-methylbutene-1 provides a series of higher molecular weight poly (carbonyl fluoride) oligomer acid fluorides without any evidence of fluoroformate formation. The fluoroformate problem, which occured with previously known methods of synthesis has been solved. Yields of hydraulic fluids are now much higher because all of the oligomer product of the reaction can be used. Under static conditions, the prior art method, which involved the oxidation of hexafluoropropene gave a 7.2% yield of poly (carbonyl fluoride) oligomer acid fluorides, while the present invention, which involves the oxidation of F-3-methylbutene-1, unexpectedly provides an approximate 46% yield. In further attempts at improving the synthesis of these desirable oligomers and in an attempt to increase their utilization in the synthesis of triazine hydraulic fluids, it was discovered that the reaction rate of the photo-oxidation of F-3-methylbutene-1 could be increased twofold by incorporating a minor amount of bis(trifluoromethyl)trioxide as a reaction initiator. Ultraviolet radiation is required in the oxidation reaction since no oxidation was observed during a 24 hour period when the reaction was attempted using a sunlamp as a light source. A fog was observed within the reaction flask as the oxidation proceeded when the reaction progressed to give the desired acid fluoride. When this phenomenon was not observed, no oxidation took place and starting materials were recovered.

The following examples are presented to further illustrate the nature of the invention and how it may be carried into effect. Although these examples depict specific embodiments of the invention, they are not to be deemed as limiting the scope of the invention in any way:

EXAMPLE I

Oxidation of F-3-methylbutene-1 using bis(trifluoromethyl) trioxide a. The thermal reaction of F-3-methylbutene-1, oxygen and bis(trifluoromethyl)trioxide (300 mm, 300 mm and 30 mm, respectively) was carried out in a 500-ml, one-necked flask. After evacuating the system, the reactants were added and placed in an oil bath at 24° C. which was then heated over a four hour period to 100° C. The pressure showed a steady increase following closely the ideal gas law. The system was maintained at 100° C. for 16 hours and infrared analysis showed no reaction to be occurring.

b. The UV initiated oxidation of F-3-methylbutene-1 in the presence of bis(trifluoromethyl)trioxide was carried out in a one-liter, one-necked flask which had been evacuated through a vacuum stopcock. The F-3-methylbutene-1 (300 mm), oxygen (300 mm) and $CF_3OOOCF_3$ (30 mm) were added and the low pressure uv light turned on. After ca. three minutes there was a small explosive decomposition which flashed, broke the lamp, and carbonized the organic materials.

c. In the next reaction attempted, a smaller amount of the initiating $CF_3OOOCF_3$ was used. A one-liter, one-necked flask was equipped with a vacuum stopcock and a low pressure uv lamp. After being evacuated to full vacuum the reactants were allowed to expand into the system as follows: F-3-methylbutene-1 (300 mm), oxygen (300 mm), and bis(trifluoromethyl)trioxide (1.5 mm). The lamp was turned on and after 22 minutes the reaction was complete. Methanol (10 cc) was added to the flask and after stirring it two minutes, 100 cc of water was added. A methanol insoluble material (1.2 g) and 1.1 g of material which fell out of the water wash were collected. The product was isolated and dried over molecular sieves. A GLC of the two fractions was encouraging. The methanol insoluble material was a mixture of higher molecular weight poly(carbonyl fluoride) oligomer esters, e.g., 4/1, 5/1, 6/1, 7/1, etc. The average was 6/1 carbonyl fluoride oligomers while the fraction which was methanol soluble was 50% methyl perfluoroisobutyrate in addition to the lower oligomers of carbonyl fluoride. The rate of the reaction had increased by a factor of ca. 2 and the average molecular weight had increased dramatically.

d. Another reaction using a larger amount of initiator was then attempted. A one-liter, one-necked flask was equipped with a low pressure uv lamp and a vacuum stopcock before being evacuated to full vacuum. The reactants [F-3-methylbutene-1 (300 mm), oxygen (300 mm) and $CF_3OOOCF_3$ (5 mm)] were allowed to expand into the system and the lamp was turned on. After the usual induction period, the reaction proceeded smoothly and rapidly and was complete in ca. 15 minutes. The reaction was worked up as in previous oxidations e.g., 10 cc of methanol was added followed by a water wash with 100 cc of water. The products were separated and dried over molecular sieves. A GLC showed the material to be ca. 60% methyl perfluoroisobutyrate and the remaining material to be the methyl esters of the carbonyl fluoride oligomers with an average n=4.

e. Another control reaction was run with F-3-methylbutene (100 mm) and an excess of oxygen (500 mm). The one-liter, one-necked flask was equipped with a low pressure uv lamp and evacuated through a vacuum stopcock. The reactants were added and the lamp turned on. After the expected induction period the reaction proceeded as expected. After ca. one hour the pressure had stopped decreasing and the products were worked up as usual. The methanol (10 cc) was added and 100 cc of water was used to wash the products. After the product was isolated and dried over molecular sieves, it was shown, by GLC to be 80% methyl perfluoroisobutyrate with the remainder being lower molecular weight carbonyl fluoride oligomeric esters.

The reaction of F-3-methylbutene-1 (200 mm), oxygen (400 mm) and bis(trifluoromethyl)trioxide (4 mm) was then attempted. The same procedure as in previous reactions was used and after the light had been on for ca. two minutes, there was a very sharp explosion which broke several pieces of glassware along with the low pressure uv lamp. The excess oxygen along with the 2% initiator (based on olefin) seem to be an undesirable situation.

In further continuation of the research effort referred to above it was also found that the addition of a minor amount of $CF_3OF$ as a reaction initiator eliminated the need for ultraviolet radiation in order to bring about the oxidation of F-3-methylbutene-1. The oxidation of F-3-methylbutene-1 was run for 20 hours using ca. 2% $CF_3OF$. The products collected included starting olefin, and some higher boiling oligomeric acid fluoride. This indicates that $CF_3OF$ is a viable initiator. This concept is further illustrated by the following example.

EXAMPLE II

Oxidation of F-3-methylbutene-1 using $CF_3OF$ a. To try to eliminate the need for uv radiation, a reaction was carried out using $CF_3OF$ as an initiator. A one-liter, one-necked flask was used as in previous reactions with a vacuum stopcock before evacuation to full vacuum. The reactants F-3-methylbutene-1 (320 mm), oxygen (320 mm) and $CF_3OF$ (1 mm) were added and after 30 minutes there was no apparent reaction by infrared analysis. More $CF_3OF$ (5 mm) added and after standing overnight the reaction was worked up as in previous reactions. After collecting the product and drying over molecular sieves, a GLC showed unreacted starting material, perfluoroisobutyrate, and some oligomeric carbonyl fluoride esters. The molecular weight was slightly higher using $CF_3OF$ than was observed in the photolytic reactions using no auxillary initiator.

b. A one-liter, one-necked flask was equipped with a low pressure uv lamp and a vacuum stopcock before being evacuated to full vacuum. The $CF_3OOOCF_3$ (5 mm) and $CF_3OF$ (4 mm) were introduced before the F-3 methylbutene-1 (290 mm) and oxygen (360 mm) were added. The lamp was turned on and after 30 minutes the reaction had stopped as observed by no further pressure decrease. The lamp was turned off and 10 cc of methanol was added and stirred for 10 minutes. The products were collected by washing the methanol solution with water, collecting the lower organic layer and drying it over molecular seives. A GLC showed an oligomeric series of methyl esters along with methyl trifluoroacetate, methyl perfluoroisobutyrate and infrared analysis gave strong methyl ester carbonyl absorption. The poly(carbonyl fluoride) oligomers had an average n=3 value.

The trioxide, $CF_3OOOCF_3$, was prepared from carbonyl fluoride and oxygen difluoride in accordance with the following reaction.

$$2\ COF_2 + OF_2 \xrightarrow{CsF} CF_3OOOCF_3$$

No thermal decomposition of the pure $CF_3OOOCF_3$ up to 200° C. was observed.

Photolytic studies using $CF_3OOOCF_3$ were carried out by oxidizing F-3-methylbutene-1 and tetrafluoroethylene. At concentrations 1.5%, the $CF_3OOOCF_3$ caused rapid explosive oxidation immediately after the uv lamp was turned on. A rapid and controlled reaction occurred at lower concentration. Static oxidations could be readily controlled at sufficiently low concentrations of initiator. Flow system work was not undertaken because of the lack of special equipment required to maintain constant precise flow of reactants.

While the invention has been described with particularity and reference to specific embodiments thereof, it is to be understood that the disclosure of the present invention is for the purpose of illustration only and is not intended to limit the invention in any way, the scope of which is defined by the appended claims.

What is claimed is:

1. In a method for preparing poly (carbonyl fluoride) oligomers comprising the steps of introducing a reaction mixture of F-3-methylbutene-1 and oxygen into an evacuated reaction vessel; subjecting said reaction mixture to a source of ultraviolet radiation for a period of time sufficent to effect a photolytic reaction between the components of said mixture; and separating the resulting reaction products; the improvement which comprises the addition of a minor amount of bis(trifluoromethyl)trioxide to said reaction mixture as a reaction initiator.

2. A method in accordance with claim 1 wherein said bis(trifluoromethyl)trioxide is added in amounts of about 0.5 to 1.5 volume percent of said F-3-methylbutene-1.

* * * * *